US00PP29962P3

(12) United States Plant Patent
Goffreda et al.

(10) Patent No.: US PP29,962 P3
(45) Date of Patent: Dec. 11, 2018

(54) PEACH TREE NAMED 'NJ358'

(50) Latin Name: ***Prunus persica* L.**
Varietal Denomination: NJ358

(71) Applicant: RUTGERS, THE STATE UNIVERSITY OF NEW JERSEY, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University of New Jersey, Brunswick, NJ (US)

( * ) Notice: Subject to any disclaimer, the term of this patent is extended or adjusted under 35 U.S.C. 154(b) by 67 days.

(21) Appl. No.: 15/530,543

(22) Filed: Jan. 26, 2017

(65) Prior Publication Data

US 2018/0213695 P1 Jul. 26, 2018

(51) Int. Cl.
*A01H 5/08* (2018.01)
*A01H 6/74* (2018.01)

(52) U.S. Cl.
USPC ..... Plt./198
CPC ..... *A01H 6/7463* (2018.05)

(58) Field of Classification Search
USPC ..... Plt./156, 180, 194, 198
See application file for complete search history.

(56) References Cited

PUBLICATIONS

Callahan Michigan Show Peach and Plum Great Lakes Expo, Plums, Pluots, Flat Peach, and Other Novel Stone Fruits Nov. 22, 2016, retrieved on May 1, 2018, retrieved from the Internet at www.glexpo.com/summaries/2016summaries/Peach-Plum.pdf, 13 pp. (Year: 2016).*

* cited by examiner

*Primary Examiner* — Susan McCormick Ewoldt
*Assistant Examiner* — Karen M Redden
(74) *Attorney, Agent, or Firm* — Patrick J. Daugherty; Daugherty & Del Zoppo Co. L.P.A.

(57) ABSTRACT

A new and distinct peach variety of *Prunus persica* named 'NJ358' is provided. This variety is distinguished from other peach varieties by its unique combination of showy flowers, large, round, freestone fruit, with an attractive red blush, over a bright yellow-orange ground color, ripening in late season, and possessing aromatic, sweet, moderately acidic flavor.

6 Drawing Sheets

Latin name of genus and species of the plant claimed: *Prunus persica* L.

Variety denomination: 'NJ358'.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of peach tree named 'NJ358'. Our new tree resulted from crossing 'Flameprince' (non-patented) as the seed parent with our proprietary peach seedling selection 'G47-99-84258' (non-patented) as the pollen parent. The new variety differs from seed parent 'Flameprince' in that the new variety produces larger fruit and that have better flavor and aromatics. The new variety differs from pollen parent 'G47-99-84258' in that the new variety has more tolerance to bacterial leaf spot and produces larger fruit that have a more uniform round shape. The resulting tree was selected when growing in a cultivated area as the 197$^{th}$ tree in the 64$^{th}$ row of Block K at a fruit research farm in Cream Ridge, N.J.

BRIEF SUMMARY OF THE INVENTION

'NJ358' differs from the related cultivar 'Autumnglo' (unpatented), in that 'NJ358' fruit are larger than the fruit of 'Autumnglo' and the trees of 'NJ358' are more tolerant of bacterial leaf spot (*Xanthomonas campestris* pv. *pruni*) than 'Autumnglo'. 'NJ358' differs from the related cultivar 'Parade' (U.S. Plant Pat. No. 2,153), in that 'NJ358' fruit have a bright yellow-orange ground color, whereas 'Parade' fruit tend to have a yellow-green ground color. The 'NJ358' variety is also distinguished from other peach varieties due to the following unique combination of characteristics:

- Produces large, nearly round, freestone fruit with a low tendency to split when adequately cropped.
- Fruit have an attractive red blush over a bright yellow-orange ground color.
- Excellent production of fruit that ripen in late season on trees with tolerance to bacterial leaf spot.
- Fruit have superior eating quality due to their aromatic, sweet, and moderately acidic flavor.

The variety was asexually reproduced at a fruit research farm in Cream Ridge, N.J. Asexual reproduction of this new variety by budding onto 'Lovell' peach seedling rootstock (non-patented) shows that the foregoing characteristics are so reproduced.

The following detailed description concerns the original tree, 'NJ358'. The original tree and asexual progeny have been observed growing in a cultivated area at a fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966 Ed.)

BRIEF DESCRIPTION OF THE DRAWINGS

This new variety is illustrated by the accompanying photographic drawings of the 'NJ358' plant at approximately six (6) years old, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
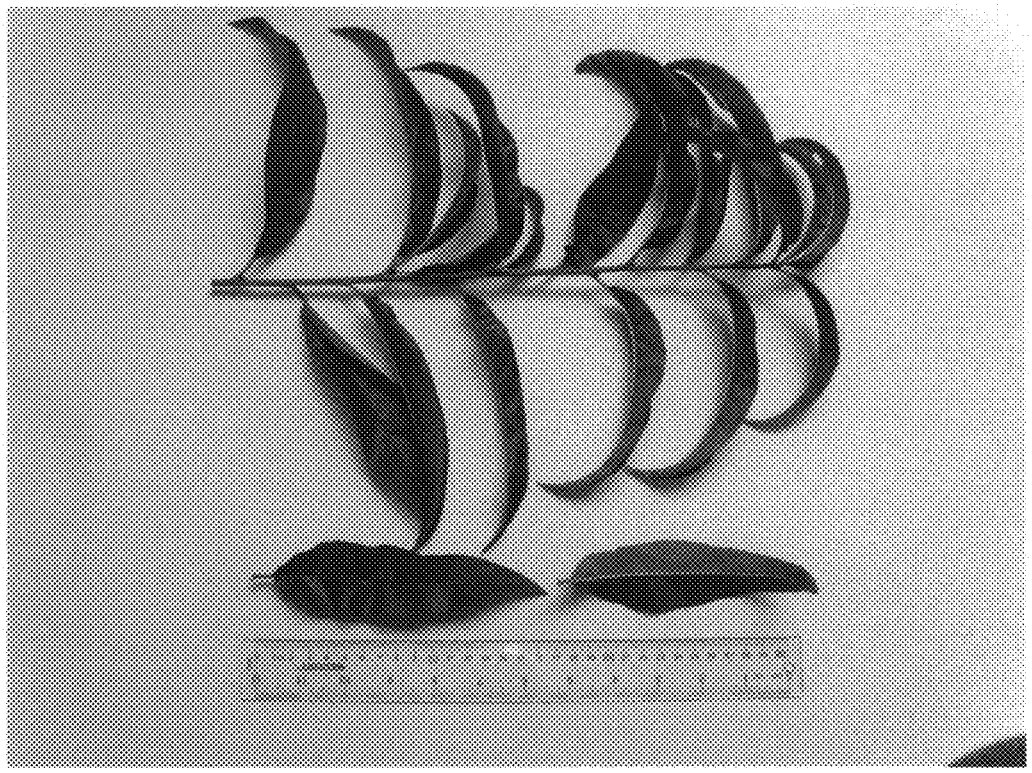
FIG. 1 is a color photograph taken on Aug. 22, 2014 of a characteristic twig of 'NJ358' in late spring bearing typical leaves of the foliage.
Figure 2:
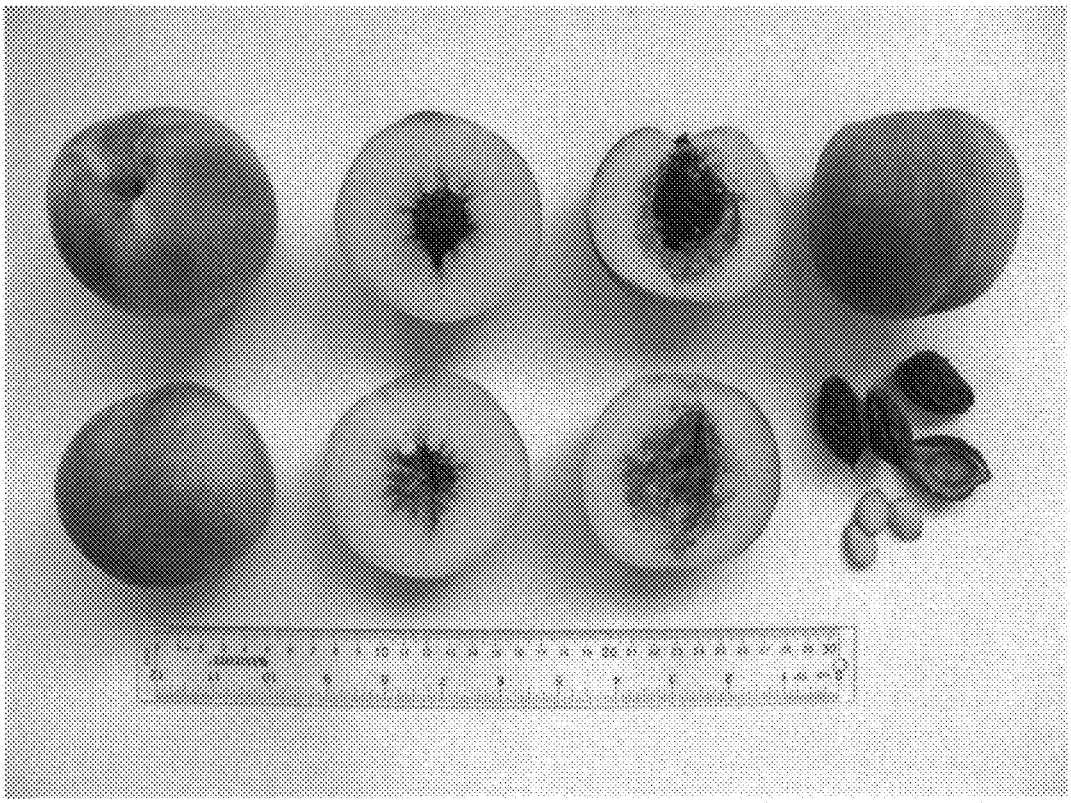
FIG. 2 is a color photograph taken on Sep. 2, 2014 of characteristic mature fruit and stones of 'NJ358'. Whole fruit are presented in three positions and both a transverse and longitudinal cross section to illustrate that the pericarp does not adhere to the pit when the fruit is mature. The stones exemplify the obovate shape and pits and grooves on the surface of the stone.
Figure 3:
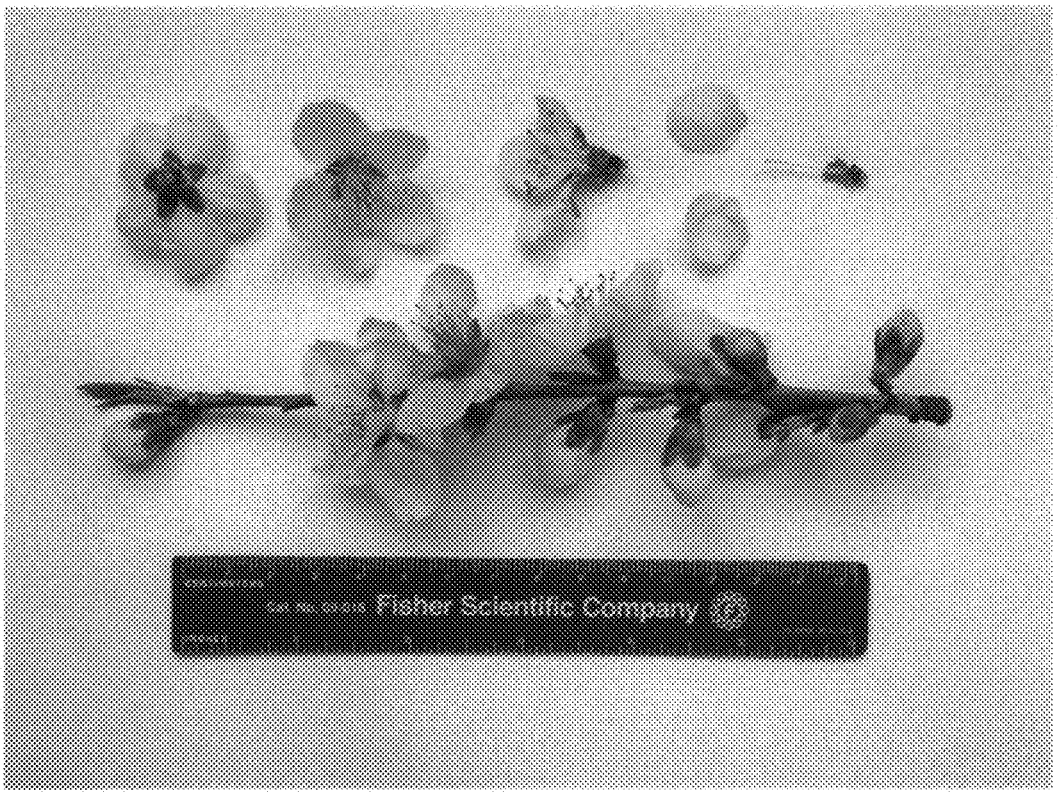
FIG. 3 is a color photograph of a characteristic twig that illustrates the typical flower buds and large, showy flowers of 'NJ358' observed on a tree at a fruit research farm in Cream Ridge, N.J. on Apr. 21, 2015.
Figure 4:
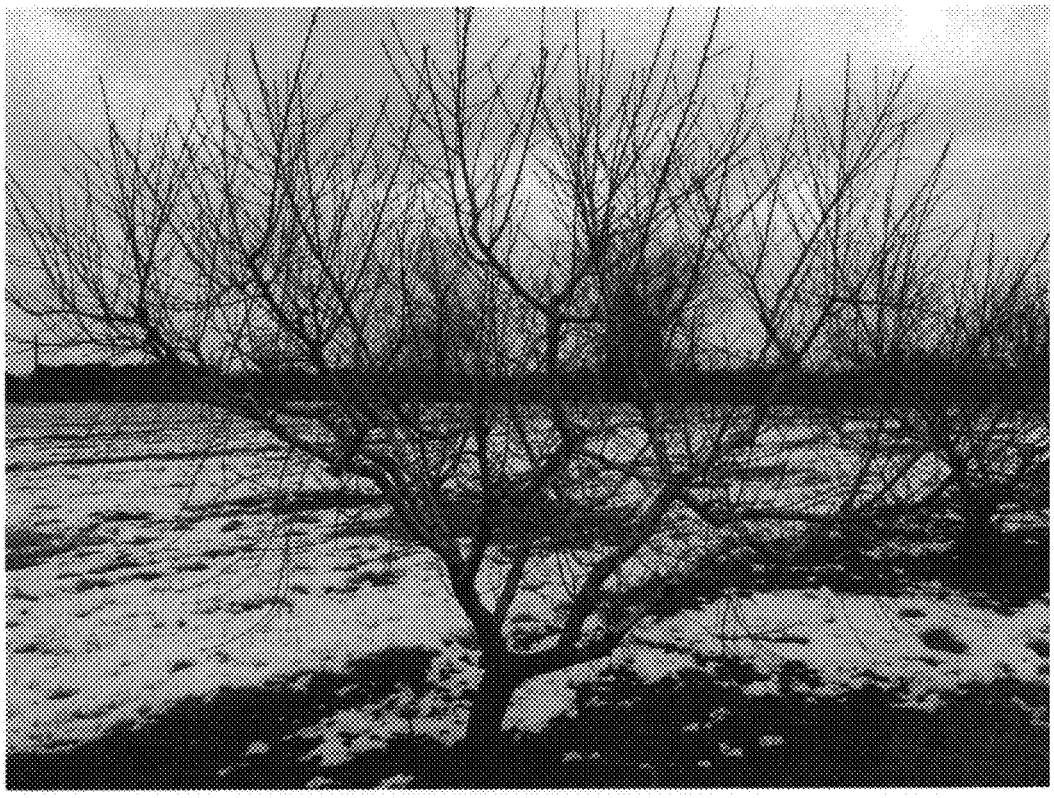
FIG. 4 is a color photograph of a dormant tree of 'NJ358', prior to pruning, in late winter that illustrates the spreading growth habit of a tree at the fruit research farm in Cream Ridge, N.J. on Feb. 8, 2016.
Figure 5:
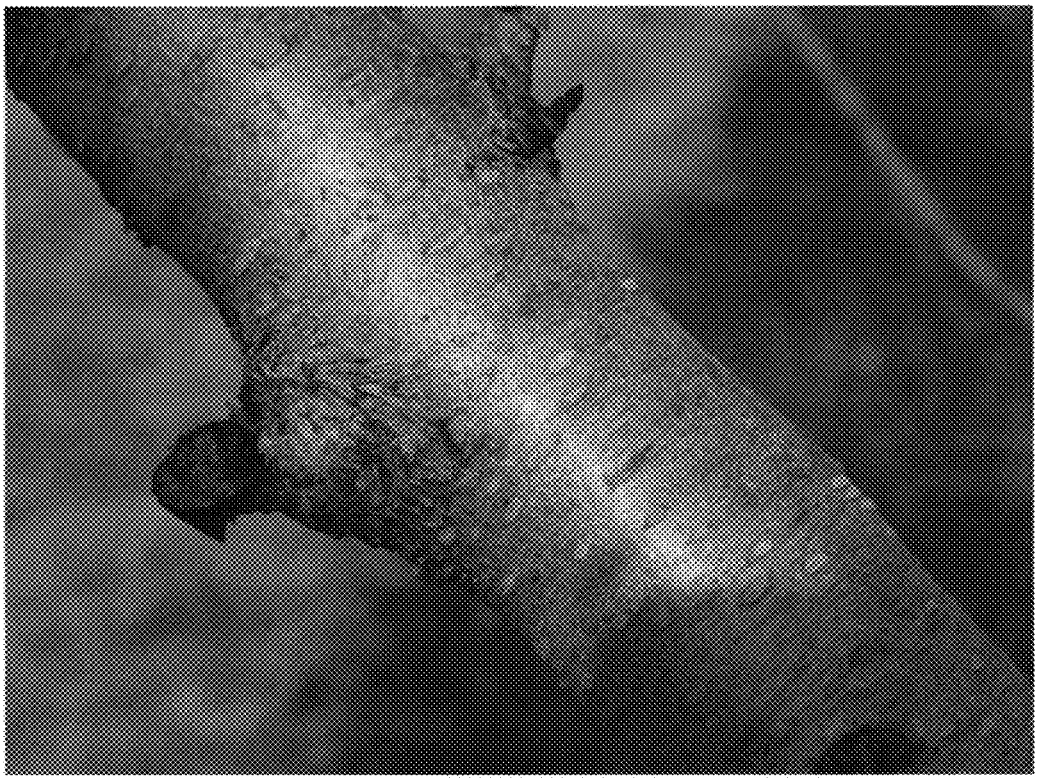
FIG. 5 is a color photograph taken on Mar. 11, 2015 of immature bark of 'NJ358' that illustrates color and the moderate density of conspicuous elliptic lenticels on the immature bark.
Figure 6:
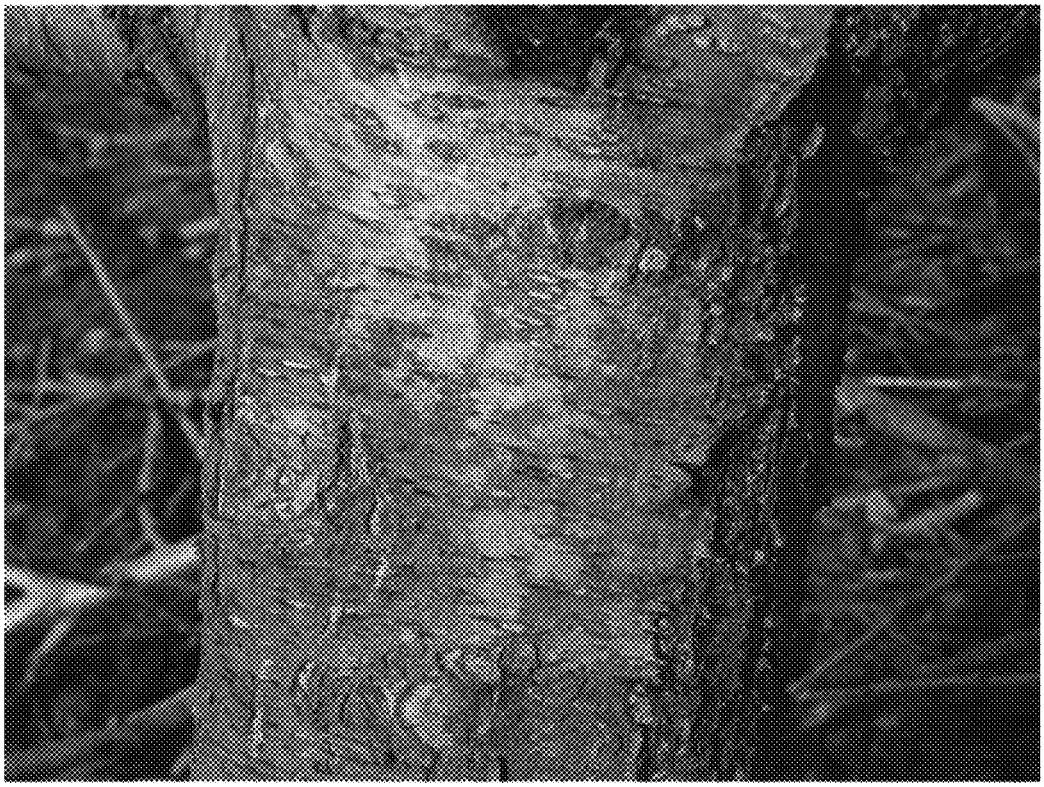
FIG. 6 is a color photograph taken on Mar. 11, 2015 of mature bark of 'NJ358' that illustrates the greyed-green color, moderately rough texture, with several shallow furrows on the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ358' variety is based on observations of an asexually reproduced tree. The observed tree was six years of age and growing on 'Lovell' seedling rootstock (non-patented) at the fruit research farm in Cream Ridge, N.J.

Scientific name: *Prunus persica* L.

Parentage:

*Seed parent*.—'Flameprince'.

*Pollen parent*.—'G47-99-84258'.

Tree:

*Vigor*.—Vigorous.

*Plant hardiness zone*.—Growth of plants has only been observed in zone 6b.

*Dormant flower bud cold tolerance*.—At least to −21° C.

*Leaf bud burst*.—Typically in mid-April when grown in Cream Ridge, N.J., but can vary by one to two weeks.

*Overall shape*.—Spreading.

*Height*.—Average as compared to other peach cultivars. For example, measurement of a typical grafted tree on 'Lovell' peach seedling rootstock (non-patented) at six years after planting shows an average height of 3.0 meters when grown in Cream Ridge, N.J.

*Width*.—Average as compared to other peach cultivars. For example, measurement of a typical grafted tree on 'Lovell' peach seedling rootstock (non-patented) at six years after planting shows an average width of 4.3 meters when grown in Cream Ridge, N.J.

*Caliper*.—Six year old tree is 41 cm. in circumference measured at 20 cm. from the ground.

Trunk and branches:

*Trunk bark texture*.—Moderately rough with several shallow furrows.

*Trunk bark color*.—Greyed-green (RHS 197C).

*Primary branches*.—Branches that are approximately 15 cm. in circumference are greyed-orange (RHS 176B) overlaid with grey (RHS 201B). Lenticels: Moderate density, approximately 0.9 per square cm; elliptical in shape and conspicuous; typical examples of which averaged 4.4 mm. in length and 2.1 mm. in width; black (RHS 202B) in color becoming greyed-orange (RHS 144B) towards the center. Branch pubescence: None. New growth bark: Greyed-purple (between RHS 183A and RHS 183B) in sun; yellow-green (RHS 152D) in shade.

*Internodes*.—Length averaging 22.4 mm. on a one-year shoot.

Leaves:

*Texture*.—Glabrous, both surfaces.

*Sheen*.—Young leaves semi-glossy with a flat finish on the underside.

*Length*.—About 160 mm. to 190 mm., averaging about 178 mm. including the petiole.

*Width*.—About 36 mm to 44 mm., averaging about 40 mm.

*Petiole*.—Averaging 10.6 mm. long and about 2.1 mm. in diameter; Color: Yellow-green (146 C).

*Margin*.—Crenate.

*Margin undulation*.—Slight.

*Form*.—Lanceolate, and concave in cross section.

*Apex*.—Sharply acuminate, curved downward.

*Base*.—Acute.

*Venation*.—Pinnate,

*Glands*.—Number: About 2 to 4, averaging about 3.3. Position: Mostly located on the petiole. Size: Length averaging 2.1 mm. and width averaging 1.1 mm. Form: Reniform.

*Stipules*.—Stipules are present on immature leaves, but they are not persistent. Typically, there are two per immature leaf, with an average length of 11.7 mm. The color is yellow-green (RHS 146 B), becoming yellow-green (152 A) just prior to dehiscence. None observed on mature leaves.

*Leaf color*.—Upper leaf surface: Yellow-green (RHS 146A). Lower leaf surface: Yellow-green (between RHS 147A and RHS 147B). Vein: Yellow-green (between RHS 150B and RHS 150C).

*Pubescence*.—None.

Flowers:

*Size*.—Large size, typical flower measuring between 37 mm. and 44 mm, averaging about 39 mm. across.

*Color*.—Dormant bud: Grey (RHS 201C) becoming Grey (RHS 201A) near the base. Pink stage bud: Red (RHS 55B). Open flower: Freshly opened flowers are red (RHS 56C) becoming red (between RHS 55B and RHS 55D).

*Petals*.—Typically five petals per flower; slightly cupped, nearly round, margin entire, averaging about 19.9 mm. long and 17.3 mm. wide. Fully expanded upper petal color red (between RHS 55B and RHS 55D). Fully expanded lower petal color red (between RHS 55B and RHS 55D).

*Petal apex*.—Obtuse, nearly rounded.

*Petal base*.—Cuneate.

*Stamens*.—Number: Variable, typical range 38 and 43, averaging 40.0. Position: Perigynous and near the point of attachment of the petals. Length: Variable, between 10.4 mm. to 13.8 mm, averaging 12.6 mm. Filament color: Greyed-green (between RHS 193C and RHS 193D). Anther color: Orange-red (between RHS 34B and RHS 34C).

*Stigma*.—Located approximately at the same level as the majority of the stamens.

*Pistil*.—Number: One. Size: Length between 18 and 22 mm, averaging 20 mm. Pistil color: Yellow-green (RHS 145A). Ovary: Moderate, long pubescence and ellipsoid in shape, color yellow-green (RHS 145A).

*Sepals*.—Number: Five. Pubescence: Length short, low to moderate density. Color: Greyed-purple (between RHS 183A and RHS 183B). Shape: Triangular, with a rounded apex. Size: Length averaging 5.5 mm., width averaging 4.8 mm.

*Nectar cup color*.—Greyed-orange (RHS 167B).

*Pollen*.—Abundant, viable and plant is typically self-fruitful; Color is yellow (RHS 11A).

*Fragrance*.—Very slight.

*Bloom season*.—Onset of bloom in 2014 on April 14; full bloom on April 21.

Fruit:

*Size*.—Large, averaging about 7.7 cm. long, 8.1 cm. wide parallel to the suture and 7.8 cm. wide perpendicular to the suture.

*Typical weight*.—262 g.

*Form*.—Longitudinal section: Nearly round to slightly lipped. Traverse section: Nearly round.

*Suture*.—Very shallow, extending from base to apex.

*Ventral surface*.—Nearly smooth at its base, becoming lipped towards the apex.

*Base*.—Round.

*Apex*.—Flat; apex tip is a small point.

*Stem*.—Average length of 7 mm. and an average diameter of 4.5 mm.

*Skin*.—Thickness: Medium. Surface: Pubescent, generally light and short. Tenacity: Medium. Astringency: None. Tendency to crack: Low. Color: Blush is red (RHS 42B); mottle and stripes are red-purple (RHS 59A); ground color is yellow-orange (between RHS 15C and RHS 15D).

*Fruit properties*.—Flesh color: Yellow-orange (RHS 14C); red (RHS 46D) adjacent to stone. Flesh firmness: Average. Flesh adhesion: Freestone. Juice: Moderate. Texture: Firm, but melting. Fibers: Not noticeable. Ripens: Between August 24 and September 6 at Cream Ridge, N.J. Flavor: Sweet, moderate acidity. Soluble solids: 11.7%. Aroma: Moderate. Eating quality: Very good.

*Keeping quality*.—Medium. Has held its flavor and firmness for at least 14 days in cold storage at 1° C. to 2° C.

*Shipping quality*.—Good. No bruising or scaring disorders have been observed.

*Usage*.—Dessert.

*Market*.—Local and long distance.

*Productivity*.—Excellent, though varies greatly depending upon conditions inclusive of winter and spring temperatures, rainfall, tree density, pruning methods, soil type, fertilization, irrigation, and degree of fruit thinning. Trees have produced a full crop in 9 out of 10 years in Cream Ridge, N.J.

Stone:

*Type*.—Freestone.

*Form*.—Obovate.

*Base*.—Medium.

*Apex*.—Medium.

*Surface*.—Pits and grooves.

*Ventral suture*.—Medium.

*Dorsal ridge*.—Medium height, medium width, forming deep lines.

*External color*.—Greyed-orange (RHS 177B).

*Cavity surface color*.—Greyed-orange (RHS 165D).

*Average stone dry weight*.—8.6 g.

*Average stone wall thickness*.—Varies between 5.5 mm. along the dorsal ridge to 10.8 mm. at the base.

*Size*.—Averages about 41.9 mm. long, 28.3 mm. wide parallel to the dorsal ridge, and 19.1 mm. wide perpendicular to the dorsal ridge.

*Tendency to split*.—Typically low when well cropped.

Kernel:

*Form*.—Elliptic to slightly obovate.

*Skin color*.—Greyed-orange (RHS 162B).

*Vein color*.—Greyed-orange (RHS 162C).

*Viability*.—Yes.

*Size*.—Averages about 19.4 mm. long, 12.9 mm. wide, and 3.7 mm. in breadth.

Plant/fruit disease and pest resistance/susceptibility: No atypical resistances/susceptibilities have been noted under normal cultural practices.

We claim:

1. A new and distinct variety of peach tree, substantially as herein shown and described.

* * * * *